(12) United States Patent
Pacey et al.

(10) Patent No.: US 9,867,531 B2
(45) Date of Patent: Jan. 16, 2018

(54) VIDEO RETRACTOR

(71) Applicant: Verathon Inc., Bothell, WA (US)

(72) Inventors: John Allen Pacey, Vancouver (CA); Mitchell Visser, Burnaby (CA); Reza Ahmadian Yazdi, Richmond (CA); Hugh Leung, Burnaby (CA); Yongkook Kim, Port Moody (CA); Rohan Sidhu, Abbotsford (CA)

(73) Assignee: Verathon Inc., Bothell, WA (US)

( * ) Notice: Subject to any disclaimer, the term of this patent is extended or adjusted under 35 U.S.C. 154(b) by 0 days.

(21) Appl. No.: 14/170,890

(22) Filed: Feb. 3, 2014

(65) Prior Publication Data
US 2014/0179998 A1    Jun. 26, 2014

Related U.S. Application Data (63) Continuation of application No. PCT/IB2012/002981, filed on Dec. 26, 2012.

(51) Int. Cl.
*A61B 1/32* (2006.01)
*A61B 17/00* (2006.01)
(Continued)

(52) U.S. Cl.
CPC ............... *A61B 1/32* (2013.01); *A61B 1/053* (2013.01); *A61B 1/267* (2013.01); *A61B 17/00234* (2013.01); *A61B 17/02* (2013.01); *A61B 17/0218* (2013.01); *A61B 17/3203* (2013.01); *A61B 90/13* (2016.02); *A61B 90/361* (2016.02); *A61B 1/0684* (2013.01);
(Continued)

(58) Field of Classification Search
CPC . A61B 17/0218; A61B 17/02; A61B 17/0206; A61B 17/0293; A61B 17/24; A61B 2017/0212; A61B 1/267; A61B 1/00105; A61B 1/32; A61B 90/13; A61B 2090/309
See application file for complete search history.

(56) References Cited

U.S. PATENT DOCUMENTS 4,947,896 A * 8/1990 Bartlett ................. A61B 1/267
600/187
5,697,891 A    12/1997 Hori
(Continued)

FOREIGN PATENT DOCUMENTS

EP    1978861 B1    10/2012
WO    2011060165 A2    5/2011

*Primary Examiner* — Matthew Lawson
*Assistant Examiner* — Amy Sipp
(74) *Attorney, Agent, or Firm* — Snyder, Clark, Lesch & Chung, LLP (57) ABSTRACT

A retractor includes a handle portion, a blade portion coupled to the handle portion. The blade portion is configured for insertion into an internal region of a patient. The blade portion includes a first portion configured to manipulate tissue of the patient. In an embodiment, a locator element is configured to highlight an external region of the patient to indicate to a user the location of the first portion in the internal region. In an embodiment, a signal-transmission medium is coupled to the blade portion and has a port. An overmolded camera unit has a lens and is configured to couple with the port. When the camera unit is coupled with the port, the lens is oriented to capture images of the internal region.

14 Claims, 11 Drawing Sheets

(51) Int. Cl.
   *A61B 17/3203* (2006.01)
   *A61B 1/267* (2006.01)
   *A61B 17/02* (2006.01)
   *A61B 1/05* (2006.01)
   *A61B 90/13* (2016.01)
   *A61B 90/00* (2016.01)
   *A61B 17/34* (2006.01)
   *A61B 1/06* (2006.01)
   *A61B 90/30* (2016.01)

(52) U.S. Cl.
   CPC .............. *A61B 2017/00455* (2013.01); *A61B 2017/3447* (2013.01); *A61B 2017/3449* (2013.01); *A61B 2090/309* (2016.02)

(56) References Cited

U.S. PATENT DOCUMENTS

| | | |
|---|---|---|
| 5,800,344 A | 9/1998 | Wood, Sr. et al. |
| 5,827,178 A | 10/1998 | Berall |
| 6,354,993 B1 | 3/2002 | Kaplan et al. |
| 6,447,527 B1* | 9/2002 | Thompson ......... A61B 17/3494 606/174 |
| 6,494,828 B1 | 12/2002 | Berall |
| 7,909,757 B2 | 3/2011 | Herman |
| 7,946,981 B1 | 5/2011 | Cubb |
| 8,029,440 B2 | 10/2011 | Birnkrant et al. |
| 8,162,826 B2 | 4/2012 | Pecherer et al. |
| 8,409,088 B2 | 4/2013 | Grey et al. |
| 2002/0029045 A1* | 3/2002 | Bonutti ............. A61B 17/0401 606/86 R |
| 2007/0049927 A1* | 3/2007 | Saltzman ........... A61B 18/1402 606/45 |
| 2007/0179342 A1 | 8/2007 | Miller et al. |
| 2011/0115891 A1 | 5/2011 | Trusty |
| 2011/0245609 A1 | 10/2011 | Laser |
| 2011/0270038 A1 | 11/2011 | Jian et al. |
| 2011/0270039 A1 | 11/2011 | Jiangming |
| 2012/0022332 A1* | 1/2012 | De Domenico ....... A61B 1/267 600/194 |
| 2012/0190929 A1 | 7/2012 | Patel et al. |
| 2012/0283718 A1* | 11/2012 | Cosmescu .......... A61B 18/1402 606/33 |
| 2014/0100620 A1* | 4/2014 | Mullaney ........... A61B 17/1725 606/86 R |

* cited by examiner

VIDEO RETRACTOR

CROSS-REFERENCE TO RELATED APPLICATIONS

This application is a continuation of PCT international application no. PCT/IB2012/002981 (formerly PCT/US2012/071615) filed on Dec. 26, 2012, which is hereby incorporated by reference in its entirety as if fully set forth herein.

BACKGROUND OF THE INVENTION

Retractors are probes used during medical procedures to provide the health care provider with controlled access to the patient and to assist with visibility of the area being treated. In general, a retractor has a control arm or blade portion that extends from a handle or base portion. The control arm or blade operably engages the area being treated, while the handle or base is used to position the control arm or blade as needed. The retractor can be hand-held by a health care provider or mounted to an examination table, operating table, or the like.

The shape of the retractor's blade portion often defines and limits its use. For example, a retractor's blade that is sized and shaped to fit down a patient's throat is often referred to as an intubation instrument or a laryngoscope. Similarly, specific use retractors, such as anoscopes and colposcopes, are retractors that have blades that are shaped to optimally engage specific areas of the patient.

Recently, efforts have been made to improve the effectiveness of some types of retractors by adding lighting and/or video systems. While such camera and lighting systems can improve the health care provider's viewing abilities of the patient, they have several drawbacks. For example, since most retractors must be sterilized prior to use, cameras, lights, and their related electronics that are secured to the retractor are regularly subjected to sterilization procedures. Over time, these procedures can tend to prematurely deteriorate these components thereby limiting their useful lives.

Similarly, since most retractors are monolithic structures having a blade that is sized and shaped for a single purpose, if a health care provider would like different use retractors to each have video and/or lighting systems, each type of retractor requires its own camera and/or lighting system to be mounted therein. Moreover, since blade sizes and shapes for a given use retractor, such as laryngoscopes, can vary, for example for use on adults and children, each different sized laryngoscope must have its own camera and/or lighting systems mounted thereto. Accordingly, despite the benefits associated with providing video and/or lighted retractors, the high number of cameras, lighting systems, their related electronic systems, and their related increased costs associated with maintaining them, significantly increases the overall costs of providing these systems to health care providers.

In addition, the camera system is typically out of service during cleaning cycles, which may impact its usefulness should an emergency need arise during the cleaning cycle.

DETAILED DESCRIPTION

One or more embodiments include a surgical retractor with a camera, redundant light, and a suction $CO_2$ channel capability. The device may include a handle ergonomically designed to provide control of the lifting arm and to conduct the electrical elements required to provide power to the lighting system and the camera, also providing a path for the video signal conduction wires to the external points of display. The superior end of the handle furthest from the blade may have a prominent projection forward that will permit application of lifting force with less effort required to hold the part. The device may also have a mounting pin that permits attachment to a retractor support arm (e.g., RoboTrac) that is present in the operating room.

The handle may also be fitted with power supply such as a rechargeable battery and/or a transmission capability for video transmission or recording. The electronic handle may have control switches or displays for capture of images.

The handle of an embodiment of the device can have a handle similar to the pistol grip frequently seen in the sport of fencing that permits thrust control and rotation control and may be of a specific dexterity, (i.e., right- and left-handed versions are available.)

The blade extension from the handle may be designed specifically for surgical task requirements for different given procedures. The width and length may be the primary variables. The blade may have special features that conform to each respective use. There can be more width, for example, in the area of the camera to prevent tissue from encroaching on the field of view/exposure of the camera and the lights. Experimentation has shown that the tissue reflects light which is detected by the camera and results in a reduction of the camera sensitivity to light. The reduced sensitivity of the camera then causes a poor image from the tissue distal to the blade tip.

The lifter (e.g., blade portion in front of the camera) may also be variable in length, width, height and shape to work in conjunction with any blade extension designed specifically for particular surgical requirements.

The blade length may reflect the size of the cavity that is being created by surgical dissection. This may be apparent by considering the difference in the case of the facelift procedure and the breast prosthesis implant. The breast dissection requires a much larger cavity and is done through a single incision in the axilla, sub areolar space, or the lower margin of the breast, whereas the facial incision is made in the mid neck and lateral to the elevated facial flap, which requires less length.

The blade may be constructed of a strong inflexible material that will allow lifting forces to be applied without deformity. The camera may be on the inferior surface of the device for such applications as breast implant cavity dissection, but in some situations, such as dissection of the prostate, the camera may be best sited on the upper surface because the blade will be holding the bladder and rectum down while the pelvic bone at the symphysis pubis is a fixed superior structure. The blade-mounted lighting may be on the same surface as the camera so that it will provide light in darkened cavities of the body.

The device includes channels for the introduction of instruments and/or passage of gases in or out of the cavity.

The tip may have "teeth" (e.g., raised bumps) on the superior surface for stabilization of the flap tissue being retracted. The stabilization teeth may be a serrated edge on the end blade. This configuration of teeth allows for tissue stabilization without the risk of catching tissue during dissection. The number and shape of teeth may also vary to provide different levels of tissue stabilization.

The blade may also have protective features to prevent camera contamination. This can be done either through a "duck bill" shape of the lifter or side walls (i.e., shielding elements) added to the bottom side of the lifter.

The blade can be interchangeable in some embodiments so that a single handle part may use several blade designs and be provided in a kit form that offers flexibility during any operative procedure. The kit may have a selection of blades for different operations.

The device can be in an autoclavable form that has a steel handle and a single-use (i.e., disposable) camera unit that can be provided sterile and attached when the sterile field is available. The camera can have electrical connections that are durable and resilient during cleaning cycles.

The device may be in a narrow form factor design that may allow penetration via 1-2 cm laparoscopic entry sites and can allow a retraction function to either give a panoramic view or a closeup micro view as required. An embodiment may further include instrumentation to assess tissue oxygenation, circulation, and/or cytological character (such as malignancy).

The device may be equipped with a tip location beacon. The beacon may be used to provide an external reference for the clinician to identify the location of the retractor tip inside a body. Depending on the surgical procedure, the location of the retractor tip may not be easily identified and such feature will aid in identifying where the retractor tip is positioned.

Figure 1:
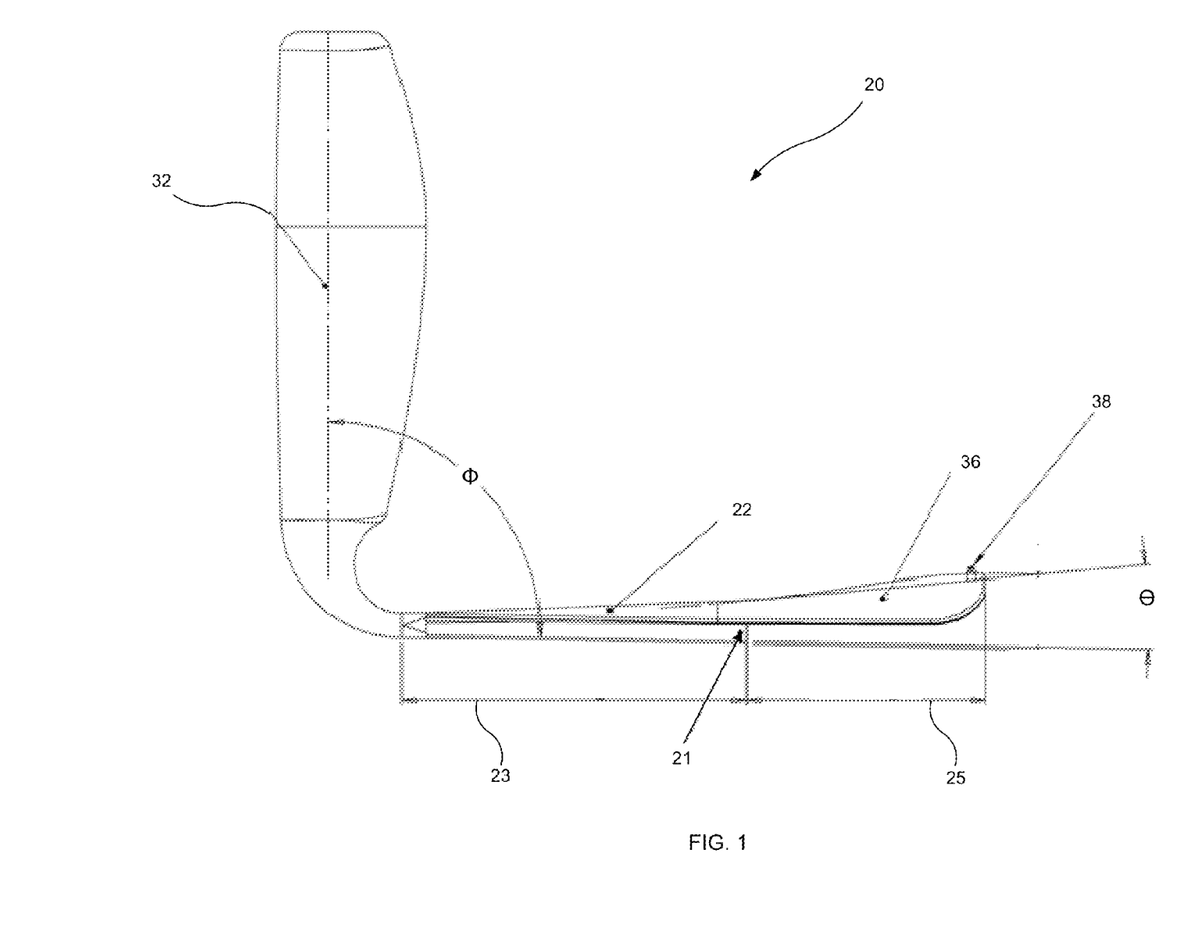
FIG. 1 is a side view of a retractor in accordance with an embodiment of the present invention.
Figure 2:
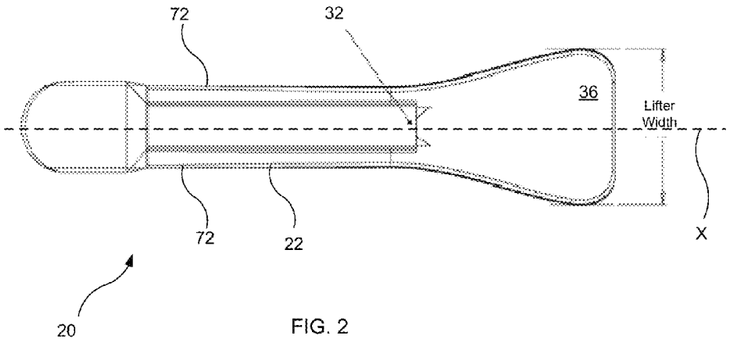
FIG. 2 is a top view of the retractor of FIG. 1.
Figure 3:
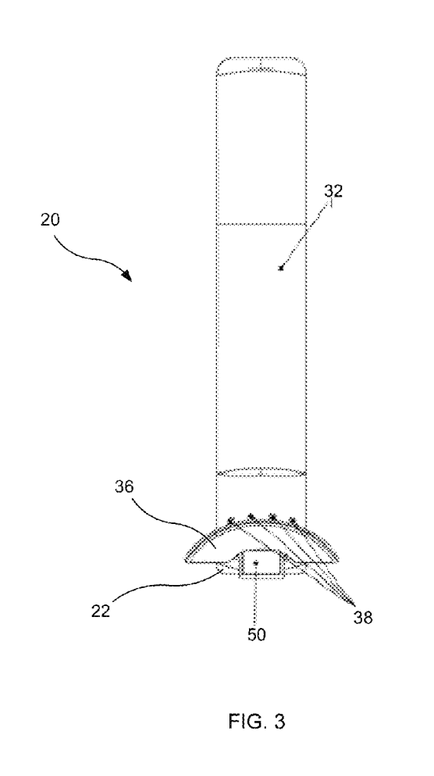
FIG. 3 is a front view of the retractor of FIG. 1.
Figure 8:
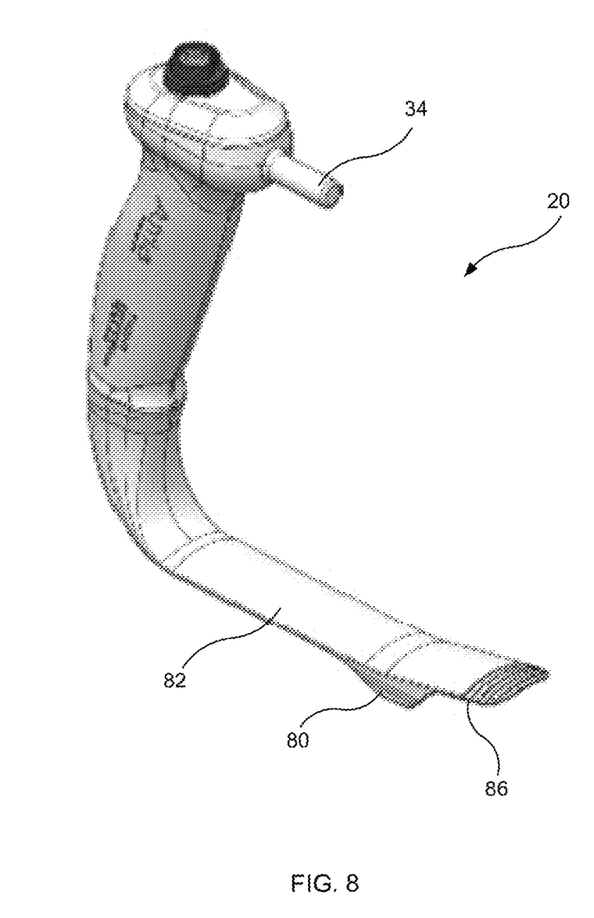
FIGS. 8-9 illustrate an alternative embodiment of the present invention.

With reference to FIGS. 1-3, a first retractor embodiment 20 is illustrated. A blade portion 22, having a length 23, is coupled to a handle portion 32 in a manner allowing an angle Φ between the blade portion 22 and handle portion 32 to be variably adjusted by a user. The blade portion 22 is preferably formed from a material that can withstand repeated sterilization such as metal, rigid plastic, or the like. In an embodiment, a rigid mounting pin 34 (FIG. 8) is also operably secured to the retractor 20, preferably at the handle portion 32, as shown.

The retractor 20 includes a lifter portion 36, having a length 25, that is configured to be inserted into an internal region (e.g., throat) of the patient. The lifter portion 36 preferably extends from the blade portion 22 at a desired defined angle θ. The lifter portion 36 may be rotatable at least 180 degrees around an axis X (FIG. 2) of blade portion 22. In an embodiment, lifter portion 36 includes a gripping surface 38 having an associated comparatively high coefficient of friction to assist in the manipulation of patient tissue. The gripping surface 38 may include, for example, one or more raised bumps or ridges.

Figure 13:
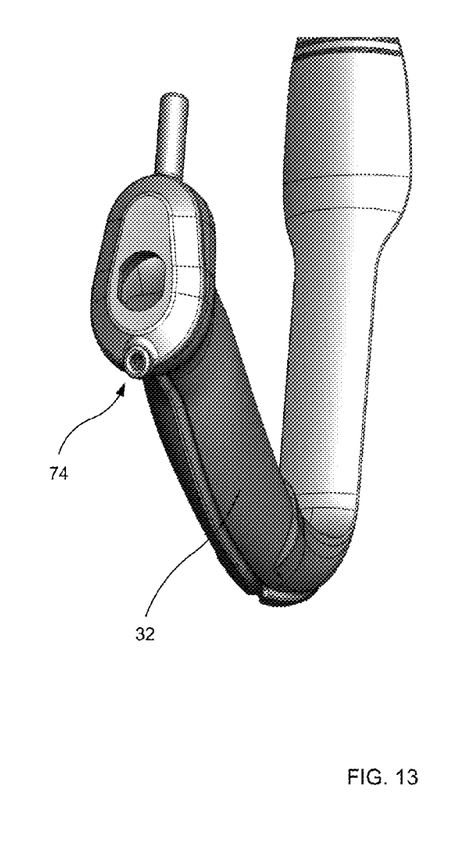
FIGS. 13-14 illustrate a retractor including a port and instrument channels according to an embodiment of the present invention.
Figure 14:
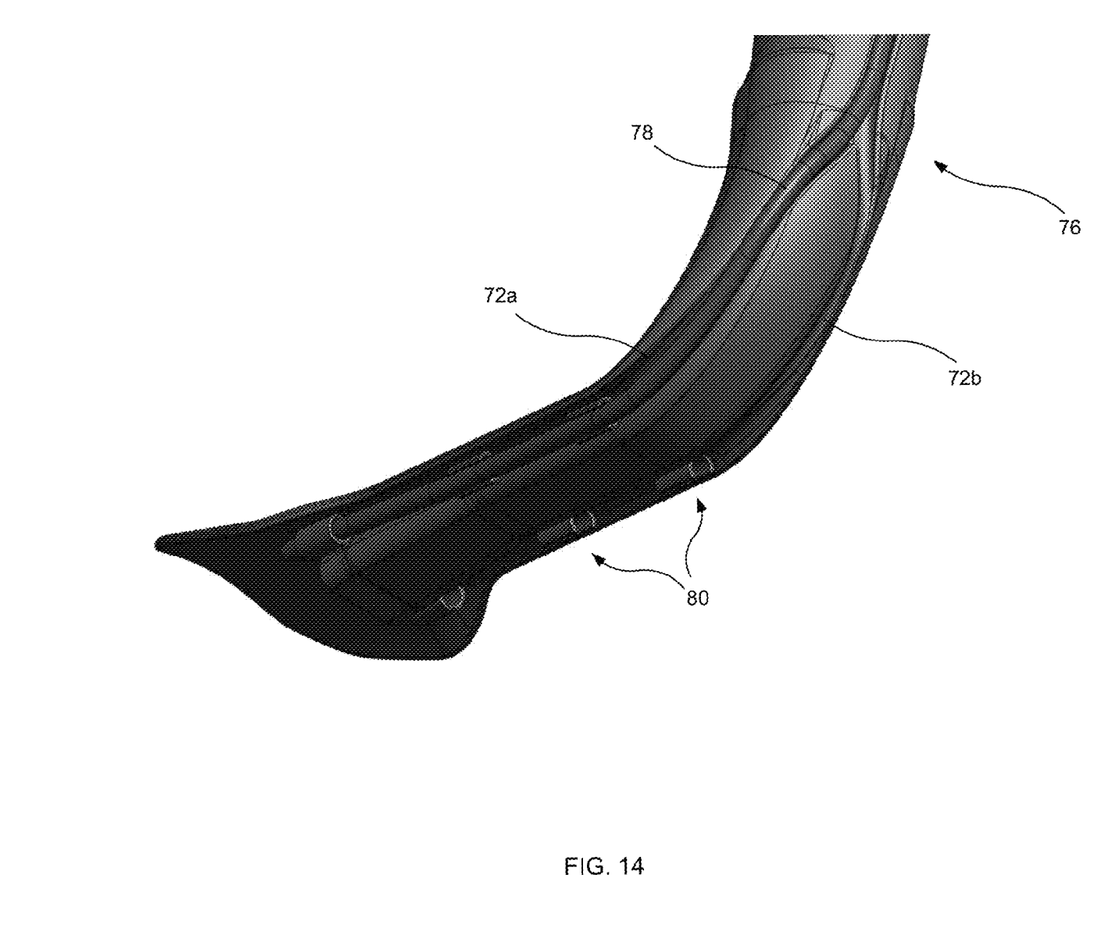

Referring to FIGS. 2 and 13-14, an embodiment of retractor 20 may include one or more channels 72 extending through handle portion 32, blade portion 22 and/or lifter portion 36 and configured to serve as a conduit through which medical devices such as a waterjet dissection instrument, suction tubes, cauterization lasers, and the like may be inserted into the internal region. As best shown in FIG. 13, such medical devices may be threaded through or to channel(s) 72 via a port 74 disposed on handle portion 32. As best shown in FIG. 14, a channel junction 76 may be formed in the handle portion 32, blade portion 22 and/or lifter portion 36 to form dual channels 72a, 72b through which multiple instruments, such as the tube 78 illustrated in FIG. 14, can traverse. In an embodiment, such instruments may be held in place along one or more portions of handle portion 32, blade portion 22 and/or lifter portion 36 by one or more clips 80.

Figure 4:
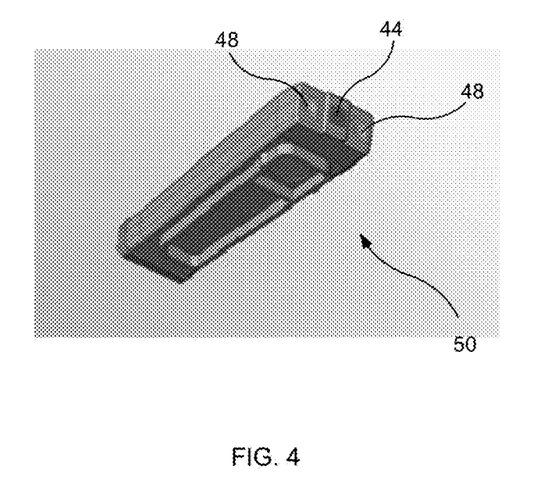
FIG. 4 is a front perspective view of a camera unit in accordance with an embodiment of the present invention.
Figure 5:
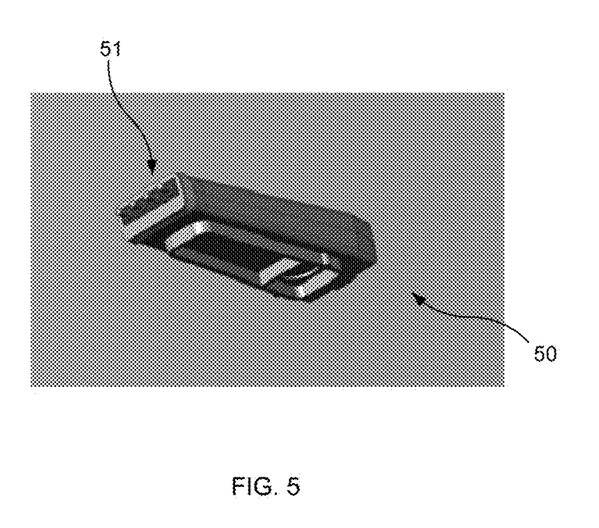
FIG. 5 is a rear perspective view of the camera unit of FIG. 4.
Figure 6:
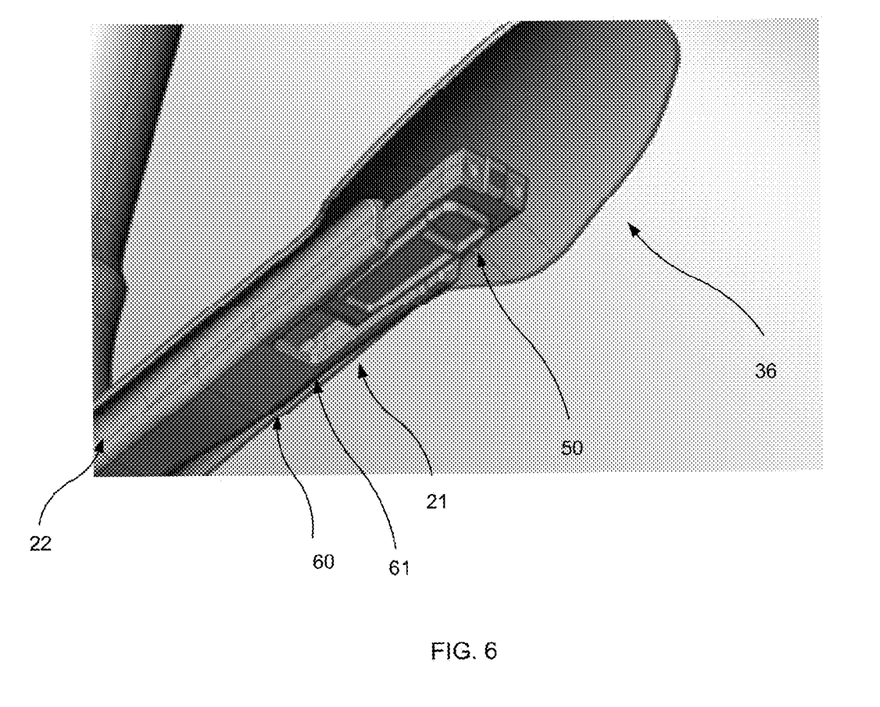
FIG. 6 is a front perspective view of the camera unit in the process of coupling with the retractor of FIG. 1.
Figure 7:
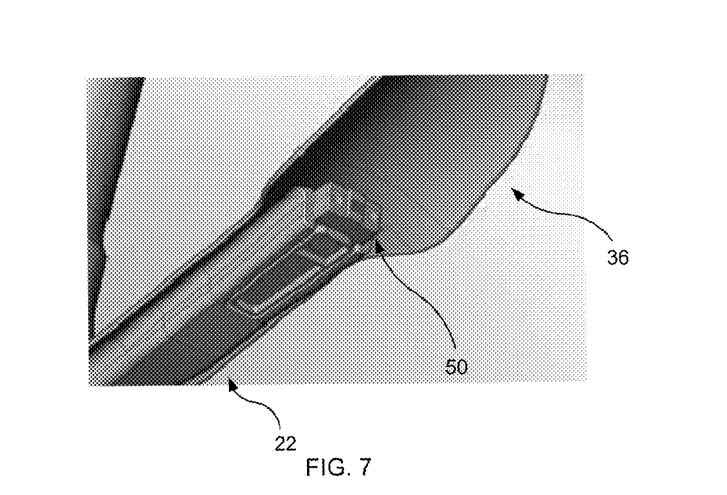
FIG. 7 is a front perspective view of the camera unit coupled with the retractor of FIG. 1.

As best illustrated in FIGS. 6-7, the blade portion 22 includes an end portion 21 distal to the handle portion 32 for detachably receiving an overmolded camera unit 50 (FIGS. 4-5) therein. The camera unit 50 preferably includes electrical pin contacts 51, a lens 44 and one or more lights 48, which are preferably Light Emitting Diodes ("LED") and are positioned around the lens to illuminate its field of view within an internal region of the patient. The use of one or more LED cold light elements in front of the camera lens 44 provides needed light without producing any discernible heat. Accordingly, unlike traditional expensive Zenon lights typically used on fiber optic laryngoscopes, economical LED lights will not burn sensitive membranes. The overmolding fabrication of the camera unit 50 serves to secure the electronics internal to the camera unit in a waterproof and sterilizable unit that will have great reliability and low cost.

The camera unit 50 may include a Complementary Metal Oxide Semiconductor ("CMOS") or Charged Coupled Device ("CCD") hybrid camera, both of which are more compact, light weight, light sensitive, and economical, than traditional cameras used in comparable applications. camera unit 50 is operable to provide images of the internal region for viewing on one or more monitors (not shown).

When placed in operational position, such as is illustrated in FIG. 7, camera unit 50 is operably connected via contacts 51 to a port 61 of a signal-transmission medium 60, such as a wireless transmitter or cable, disposed within, or otherwise coupled to, blade portion 22 at or near end portion 21. The medium 60 may include a power source (not shown), such as a battery or NC connection, needed for operation of camera unit 50.

Figure 9:
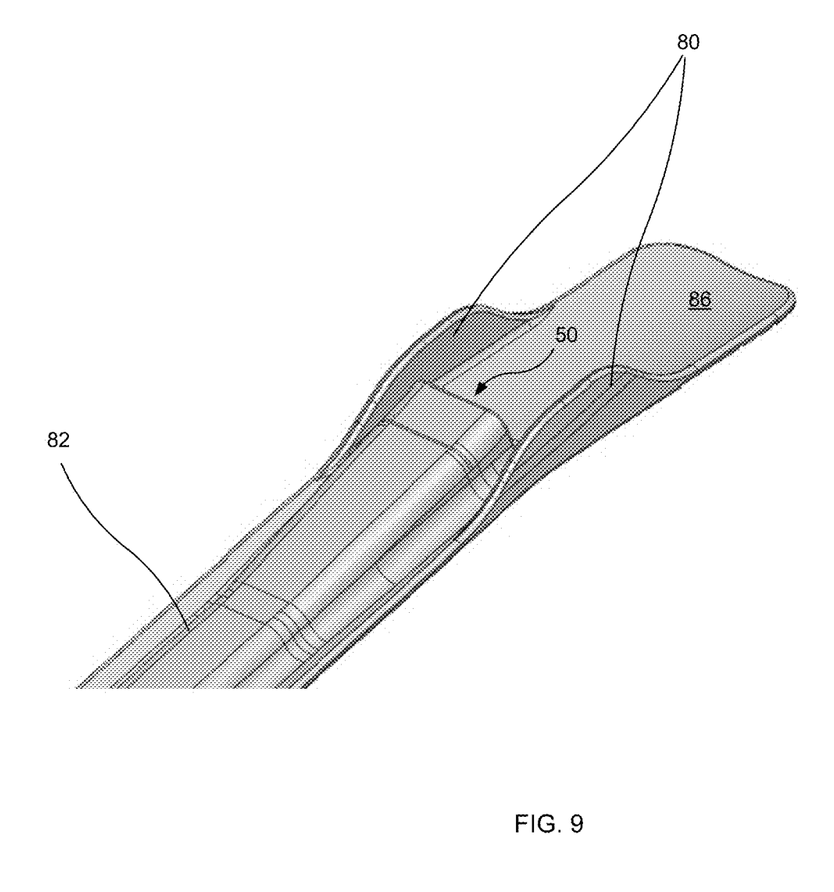

Lifter portion 36 and/or blade portion 22 may be configured, or otherwise include protective features, to prevent obstruction of a field of view of the lens 44. For example, referring to FIGS. 1-3 and 6-7, lifter portion 36, according to an embodiment, may have a "duck-bill" configuration (i.e., tapering width, as seen from top view in FIG. 2, with convex tissue-engagement surface) such that camera unit 50 may be coupled to port 61 and disposed within the shelter created by the concave region of lifter portion 36. Such shelter serves to reduce or prevent view obstruction caused by tissue and fluids lateral to movement of blade portion 22. For similar purposes, and referring to FIGS. 8-9, a combination blade portion 82 and lifter portion 86, according to an alternative embodiment, may include side walls (i.e., shielding elements) 80 laterally coupled to one or more of blade portion 82 and lifter portion 86. As can best be seen in FIG. 9, a camera unit 50 may thus be disposed within the shelter created by the lifter portion 86 and side walls 80. In an embodiment, one of side walls 80 may be smaller in one or more dimensions (e.g., length, width, etc.) than the other side wall to better facilitate manipulation of one or more medical devices at or near the lifter portion 86. It should be noted that lifter portion 86 may have the duck-bill configuration of lifter portion 36, as well.

Figure 10:
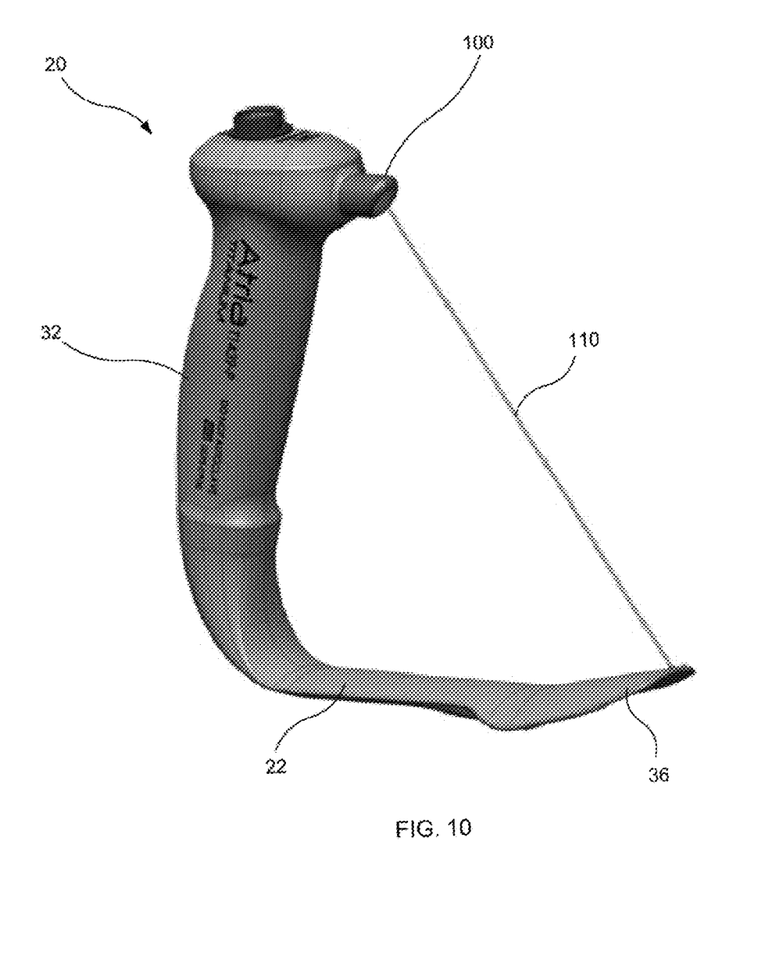
FIG. 10 is a front perspective view of the retractor of FIG. 1 including a tip location beacon according to an embodiment.

Referring to FIG. 10, retractor 20 may include a locator element 100. Upon insertion of blade portion 22 into an internal region of a patient, element 100 is configured to highlight an external region of the patient to indicate to a user the location in the internal region of a portion of blade portion 22 or lifter portion 36 chosen by the user. In an embodiment, and as illustrated in FIG. 10, locator element 100 may be a laser pointer or other illuminating device mounted to handle portion 32 and operable to generate a beam 110 to illuminate an external region of a patient. Alternatively, locator element 100 may be, for example, a conventional sight-alignment aid such as a cross-hair indicator disposed on or within handle portion 32.

In operation, for example, the user can configure the element 100 to focus on gripping surface 38 of lifter portion 36. Consequently, upon insertion of the blade portion 22 into a patient's throat, the user can track the movement of gripping surface 38 relative to the exterior of the patient by tracking the movement along the patient's neck of the laser highlight generated by element 100.

Element 100 is preferably rotationally and translationally movable so as to allow a user to choose the portion of blade portion 22 or lifter portion 36 on which locator element 100 is focused. Additionally, as angle Φ between handle portion 32 and blade portion 22 is adjusted, locator element 100 may be correspondingly manually or automatically tilted so as to maintain illumination of the chosen portion of focus.

Figure 11:
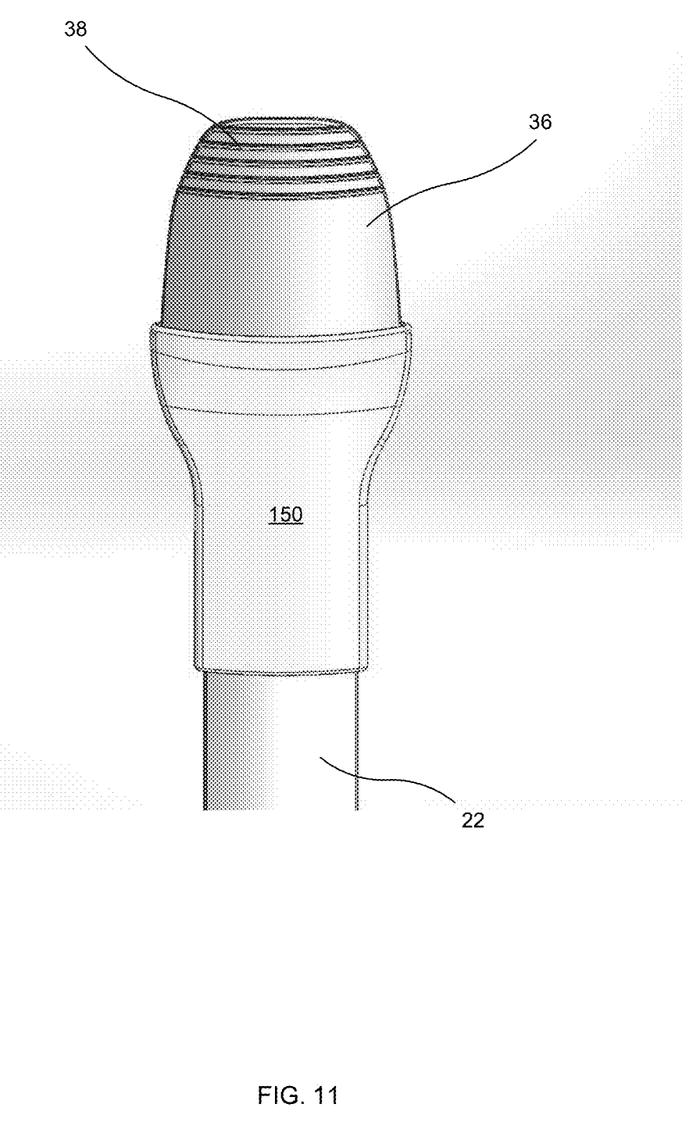
FIGS. 11-12 illustrate a carapace according to an embodiment attached to the retractor of FIG. 1.
Figure 12:
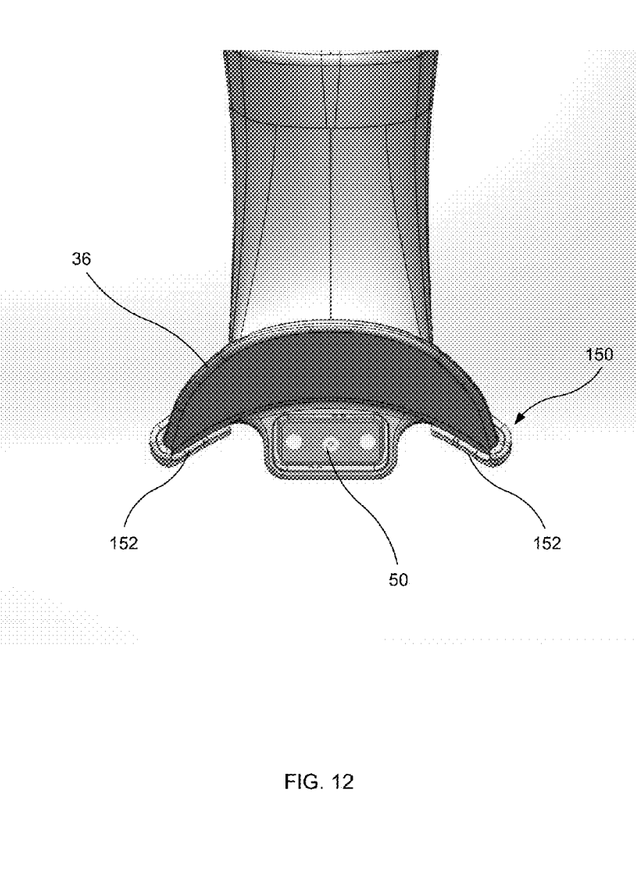

As illustrated in FIGS. 11-12, an embodiment may include a carapace 150 that removably attaches to the lifter portion 36 and, consequently, may be configured to be disposable. As best seen in FIG. 12, the carapace 150 may include clasping arms 152 functioning to grip lifter portion 36. Carapace 150 may be composed of plastic or other appropriate material that dissipates heat or otherwise provides a temperature barrier to protect tissue from thermal energy generated by retractor 20 when in use for a protracted period of time. Carapace 150 may further include serrations or projections (not shown), similar to that of surface 38, so as to offer increased tissue-gripping capability.

While the present invention has been described in terms of preferred embodiments, it will be appreciated by one of ordinary skill that the spirit and scope of the invention is not limited to those embodiments, but extend to the various modifications and equivalents as defined in the appended claims.

We claim:

1. A retractor, comprising:
   a handle portion;
   a blade portion coupled to the handle portion, the blade portion configured for insertion into an internal region of a patient, the blade portion including a first portion comprising an end of the blade portion located distally with respect to the handle portion, and configured to manipulate tissue of the patient, wherein the blade portion is not planar with respect to the handle portion; and
   a locator element coupled to the handle portion and configured to illuminate an external region of the patient, the illuminated external region indicating to a user the location of the end of the blade portion located in the internal region of the patient when the external region prevents the first portion of the blade portion from being visible to the user,
   wherein the locator element includes a light source aligned with the end of the blade portion and not aligned with the handle portion, wherein the light source is configured to illuminate a portion of the external region of the patient corresponding to the end of the blade portion located in the internal region of the patient, and
   wherein the locator element is automatically adjustable to maintain alignment of the locator element with the end of the blade portion when an angle between the handle portion and the blade portion is changed.

2. The retractor of claim 1, wherein the handle portion and blade portion are coupled to allow adjustability of an angle between the handle portion and blade portion.

3. The retractor of claim 1, wherein the first portion comprises a surface configured to grip the patient tissue.

4. The retractor of claim 3, wherein the surface configured to grip the patient tissue is located at the end of the blade portion and comprises a plurality of projections, ridges or serrations.

5. The retractor of claim 1, wherein the blade portion includes a proximal portion directly coupled to the handle portion and having an axis, and the first portion is rotatable at least 180 degrees around the axis.

6. The retractor of claim 1, wherein the blade portion comprises at least one channel configured to serve as a conduit through which a surgical instrument may be inserted into the internal region.

7. The retractor of claim 6, wherein the surgical instrument comprises a waterjet dissection instrument.

8. The retractor of claim 1, further comprising a camera unit coupled to the blade portion and oriented to capture images of the internal region proximal to the first portion.

9. The retractor of claim 8, wherein the blade portion comprises a plurality of shielding elements configured to prevent obstruction of a field of view of the camera unit.

10. The retractor of claim 1, wherein the locator element is manually adjustable to allow the user to align the light source with portions of the blade portion other than the end of the blade portion.

11. The retractor of claim 1, wherein the locator element is manually adjustable to allow the user to align maintain alignment of the locator element with the end of the blade portion.

12. A retractor, comprising:
    a handle portion;
    a blade portion coupled to the handle portion, the blade portion configured for insertion into an internal region of a patient, the blade portion comprising an end of the blade portion located distally with respect to the handle portion, and configured to manipulate tissue of the patient, wherein the blade portion is not planar with respect to the handle portion; and
    an illuminating locator element located at a first end of the handle portion and distally with respect to the blade portion, wherein the illuminating locator element is configured to highlight an external region of the patient, the highlighted external region indicating to a user the location of the end of the blade portion located in the internal region when the external region prevents the end of the blade portion from being visible to the user,
    wherein the illuminating locator element includes a light source aligned with the end of the blade portion and not aligned with the handle portion, wherein the light source is configured to illuminate a portion of the external region of the patient corresponding to the end of the blade portion located in the internal region of the patient, and
    wherein the illuminating locator element is automatically adjustable to allow a user of the retractor to maintain illumination, by the light source, of the portion of the external region of the patient corresponding to the end of the blade portion located in the internal region of the patient when an angle between the handle portion and the blade portion is changed.

13. The retractor of claim 12, wherein the illuminating locator element comprises a laser pointer.

14. A retractor, comprising:
a handle portion;
a blade portion coupled to the handle portion, the blade portion configured for insertion into an internal region of a patient, the blade portion including a first portion configured to manipulate tissue of the patient; and
an adjustable locator element configured to allow a user to maintain alignment of the adjustable locator element with the first portion of the blade portion and to illuminate an external region of the patient, the illuminated external region indicating to the user the location of the first portion in the internal region when the external region prevents the first portion from being visible to the user, and
wherein the adjustable locator element is automatically adjustable to maintain alignment of the adjustable locator element with the first portion of the blade portion when an angle between the handle portion and the blade portion is changed.

\* \* \* \* \*

UNITED STATES PATENT AND TRADEMARK OFFICE
CERTIFICATE OF CORRECTION

PATENT NO.       : 9,867,531 B2                                      Page 1 of 1
APPLICATION NO.  : 14/170890
DATED            : January 16, 2018
INVENTOR(S)      : John Allen Pacey et al.

It is certified that error appears in the above-identified patent and that said Letters Patent is hereby corrected as shown below:

In the Claims

Claim 11, at Column 6, Lines 36-37, delete the phrase "maintain alignment of".

Signed and Sealed this
Tenth Day of April, 2018

Andrei Iancu
*Director of the United States Patent and Trademark Office*